United States Patent
Wall

(10) Patent No.: US 12,257,756 B2
(45) Date of Patent: *Mar. 25, 2025

(54) METHOD FOR PRODUCING A CLINICAL WASTE CONTAINER BY INJECTION MOULDING WITH A HEATED NOZZLE

(71) Applicant: FrostPharma AB, Eskilstuna (SE)

(72) Inventor: Peter Wall, Eskilstuna (SE)

(73) Assignee: FrostPharma AB, Danderyd (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/707,179

(22) PCT Filed: Nov. 7, 2022

(86) PCT No.: PCT/SE2022/051031
§ 371 (c)(1),
(2) Date: May 3, 2024

(87) PCT Pub. No.: WO2023/080835
PCT Pub. Date: May 11, 2023

(65) Prior Publication Data
US 2024/0335990 A1   Oct. 10, 2024

(30) Foreign Application Priority Data
Nov. 8, 2021 (SE) .................................. 2151368-4

(51) Int. Cl.
*B29C 45/73* (2006.01)
*A61B 50/00* (2016.01)
(Continued)

(52) U.S. Cl.
CPC .......... *B29C 45/73* (2013.01); *B29C 45/0001* (2013.01); *B29C 45/0005* (2013.01);
(Continued)

(58) Field of Classification Search
CPC ............ B29C 45/0001; B29C 45/0005; A61B 50/3001; A61B 50/36; A61B 50/362;
(Continued)

(56) References Cited

U.S. PATENT DOCUMENTS 2,625,306 A   1/1953   Murphy
3,282,477 A   11/1966  Henchert
(Continued)

FOREIGN PATENT DOCUMENTS

DE   20309847 U    11/2003
EP   1380316 A1   1/2004
(Continued)

OTHER PUBLICATIONS

Office Action issued on May 12, 2022 by the Swedish Intellectual Property Office.
(Continued)

*Primary Examiner* — Jeffrey M Wollschlager
(74) *Attorney, Agent, or Firm* — Noréns Patentbyrå AB

(57) ABSTRACT

Clinical waste container (100) comprising
a lower basket part (110) and an upper lid part (120), comprising a cylindrical part (121) having an upper lid opening (122); and
a lid cap part (130), arranged to be fastened to said lid part so as to cover said lid opening,
wherein the lid part and the lid cap part each comprise cooperating snap-lock means (123, 133), comprising several separated elongated protrusions (133a,133b), together defining a broken circle.

The lid part comprises at a lower end (124) a bend (125) of at least 60°, with an inner radius (R1) of at the most 5 mm and an outer radius (R2) of at the most 5 mm, defining a local material thickness increase of at least 25%.

The lid part and the lid cap part comprise at least 30% by volume wooden fibres.

(Continued)

The invention also relates to a method of manufacturing such a container.

12 Claims, 9 Drawing Sheets

(51) Int. Cl.
*A61B 50/36* (2016.01)
*B29C 45/00* (2006.01)
*B29C 45/74* (2006.01)
*B29K 311/14* (2006.01)
*B29L 31/00* (2006.01)
*B29L 31/56* (2006.01)

(52) U.S. Cl.
CPC ...... *B29C 45/74* (2013.01); *A61B 2050/0083* (2016.02); *A61B 50/362* (2016.02); *A61B 2050/364* (2016.02); *B29K 2311/14* (2013.01); *B29K 2905/12* (2013.01); *B29K 2995/007* (2013.01); *B29K 2995/0097* (2013.01); *B29L 2031/565* (2013.01); *B29L 2031/712* (2013.01)

(58) Field of Classification Search
CPC .... A61B 50/37; A61B 50/39; B29D 99/0096; B29L 2031/56; B29L 2031/565; B29L 2031/712–7172
See application file for complete search history.

(56) References Cited

U.S. PATENT DOCUMENTS

| | | | |
|---|---|---|---|
| 4,288,066 A | 9/1981 | Treace | |
| 4,520,926 A | 6/1985 | Nelson | |
| 4,600,112 A | 7/1986 | Shillington et al. | |
| 5,167,193 A * | 12/1992 | Withers | A61B 50/362 206/570 |
| 5,245,117 A * | 9/1993 | Withers | A61M 5/002 405/129.55 |
| 5,249,680 A | 10/1993 | Shillington | |
| 5,259,501 A * | 11/1993 | Withers | A61M 5/3205 206/370 |
| 5,385,105 A * | 1/1995 | Withers, Jr. | F23G 5/448 110/238 |
| 5,725,121 A | 3/1998 | Gianpaolo | |
| 5,941,385 A | 8/1999 | Barton | |
| 6,010,444 A | 1/2000 | Honeycutt et al. | |
| 6,062,001 A | 5/2000 | Kunik | |
| 8,038,025 B2 | 10/2011 | Stark et al. | |
| 2002/0000683 A1* | 1/2002 | Sears | B29C 48/022 428/300.1 |
| 2004/0056040 A1 | 3/2004 | Ziegler | |
| 2005/0247714 A1 | 11/2005 | Backes et al. | |
| 2006/0219718 A1 | 10/2006 | Finnestad | |
| 2009/0283526 A1* | 11/2009 | Pierce | B65D 43/022 220/789 |
| 2012/0248129 A1 | 10/2012 | Yoshida et al. | |
| 2015/0174803 A1* | 6/2015 | Newman | B29C 45/14811 264/40.1 |
| 2016/0355909 A1 | 12/2016 | Tidesten et al. | |
| 2020/0369438 A1 | 11/2020 | Fish | |
| 2023/0097812 A1 | 3/2023 | Suzuki et al. | |

FOREIGN PATENT DOCUMENTS

| | | |
|---|---|---|
| JP | 7184961 A | 12/2022 |
| WO | 2007130402 | 11/2007 |

OTHER PUBLICATIONS

International search report issued on Nov. 22, 2022 by the ISA.
Internet citation URL: https://web.archive.org/web/20200809205554/ https://ww.apotea.se/kanylburk-2.2-liter.
International Preliminary Report on Patentability issued on Aug. 28, 2023 by the IPEA.
International search report issued on Nov. 30, 2022 by the ISA. https://web.archive.org/web/20210514153554/https:/www.sharp-container.com/sharps-container-r3b.html.

* cited by examiner

METHOD FOR PRODUCING A CLINICAL WASTE CONTAINER BY INJECTION MOULDING WITH A HEATED NOZZLE

The present invention relates to a clinical waste container and to a method for producing the same. Such container can be for disposing needles and other sharp waste (a so called sharps container), or for other clinical/medical waste.

Clinical or medical waste, such as used syringe needles, constitute a hazard and needs to be handled according to certain safe protocols. Normally, hospital personnel and other caregivers put such waste material in dedicated containers, in the form of lidded buckets or baskets, for transport to a facility and subsequent destruction.

Normally, the container is a disposable container, intended for one-time use only.

A number of requirements are put on such containers:

They need to be sufficiently resistant to externally applied abrasive wear and violent force, and also so that disposed waste in the container does not run the risk of protruding out from the container.

They need to be stackable in several stories without breaking.

They need to be available in standard volume sizes.

They need to comprise a lid that can be removed but that will not come off by accident during handling.

They need to provide an interface (such as a needle or blade disconnector) allowing caregivers to quickly and safely dispose of syringe needles and other medical waste material using only one hand. This may include disposing of such a needle by holding the syringe and twisting or turning it, using the lid as a resistance, so that the needle comes loose, in turn subjecting the lid to bending forces that it must be able to withstand.

They need to be sealable both temporarily and permanently.

They need to be completely self-contained, meaning that no loose parts should be present that can be lost during handling.

They need to be manufacturable in a simple process having high throughput.

Since such containers are manufactured in large volumes, it is important that the cost of producing them is low.

Conventionally, such containers are manufactured from plastic material, such as polypropylene. This is an inexpensive material that can be injection moulded to a desired shape, forming a durable container.

However, in order to lower the climate footprint associated with such containers, it is desirable to produce them using a material that carries lower amounts of fossil-sourced carbon. Destruction is typically via incineration, and re-use or recycling is typically not possible.

It has turned out to be difficult to achieve such a container in such material, while still fulfilling all the above requirements.

The present invention solves the above described problems, and proposes to manufacture a clinical waste container using a bio-composite material, especially a material being a mixture of wooden fibres and a plastic material. More particularly, the present invention proposes to arrange such a clinical waste container in specific ways so as to fulfil said requirements.

Hence, the invention relates to a clinical waste container being associated, in an upright operating orientation of the clinical waste container, with an upwards axial direction, an outwards radial direction and an angular direction, the clinical waste container comprising a lower basket part, having an upper basket opening; an upper lid part, arranged to be fastened to said basket part so as to cover said basket opening, the lid part comprising a cylindrical part having an upper lid opening arranged to receive clinical waste through said lid opening into said basket part; and a lid cap part, arranged to be fastened to said lid part so as to cover said lid opening, the lid cap part comprising a cylindrical part having a closed upper end and an inner dimension being larger than an outer dimension of said cylindrical part of the lid part, the cylindrical part of the lid cap part being arranged to be slid onto the cylindrical part of the lid part so that the lid cap part as a result covers the lid opening, wherein the cylindrical part of the lid cap part comprises inner snap-lock means arranged to engage with outer snap-lock means arranged on the cylindrical part of the lid part so as to fasten the lid cap part on the lid part by the material of at least the lid cap part deforming elastically into a snap-fit lock, which container is characterised in that the inner snap-lock means comprises several separated elongated protrusions, running in the angular direction in relation to the lid cap part and together defining a broken circle, in that the outer snap-lock means comprises an elongated recess, running in the angular direction in relation to the lid part and being arranged to, by at least the material of the lid cap part elastically deforming, engage with said protrusions by said protrusions protruding into said recess along a respective angular extension of said protrusions and said recess, respectively, so as to form a first snap-fit lock, in turn fastening the lid cap part to the lid part, in that the lid part comprises at a lower end of its cylindrical part a bend at which the cylindrical part of the lid part changes direction at least 60° as seen in a cross-section including a centre axially extending axis of the cylindrical part of the lid part, the bend having an inner radius of curvature of at the most 5 mm and an outer radius of curvature of at the most 5 mm, in that the material thickness of the lid part is at least 25% thicker locally at said bend as compared to a material thickness adjacent to the bend in said cylindrical part of the lid part, and in that the lid part and the lid cap part are made from a plastic material comprising at least 30% by volume wooden fibres.

Moreover, the invention relates to a method for producing a clinical waste container of said type, wherein the method comprises providing a metal mould and a heated nozzle; injecting molten plastic material comprising at least 30% by volume wooden fibres via said heated nozzle into said mould; allowing the plastic material to harden by cooling to form said lid part; removing the lid part from the mould; and providing said basket part.

In the following, the invention will be described in detail, with reference to exemplifying embodiments of the invention and to the enclosed drawings, wherein:

FIG. 1 is a perspective view of a first clinical waste container 100 according to the present invention, including a basket part 110 and a lid part 120. The view in FIG. 1 is partly exploded. It is noted that the lid part 120 is connected to a lid cap part 130, via a connecting part 140 that is shown as straight in FIG. 1. The connecting part 140 is moulded in this straight orientation, but during use the connecting part 140 may be bent 180° so that the lid cap part 130 is brought, upside down, onto the lid part 120 so as to seal a lid opening 122 of the lid part 120. Herein, an operating orientation is referred to, in which the clinical waste container 100 is in an upright position with the lid part 120 mounted on the basket part 110. This orientation is shown (albeit the lid part 120 exploded upwards in relation to the basket part 110) in FIG. 1. It is then noted that the connecting part 140 may or may not, in this operating orientation, be bent so as to allow the lid cap part 130 to reach and cover the lid opening 122. A coordinate system A, R, V is shown in FIG. 1 for reference.

Figure 1:
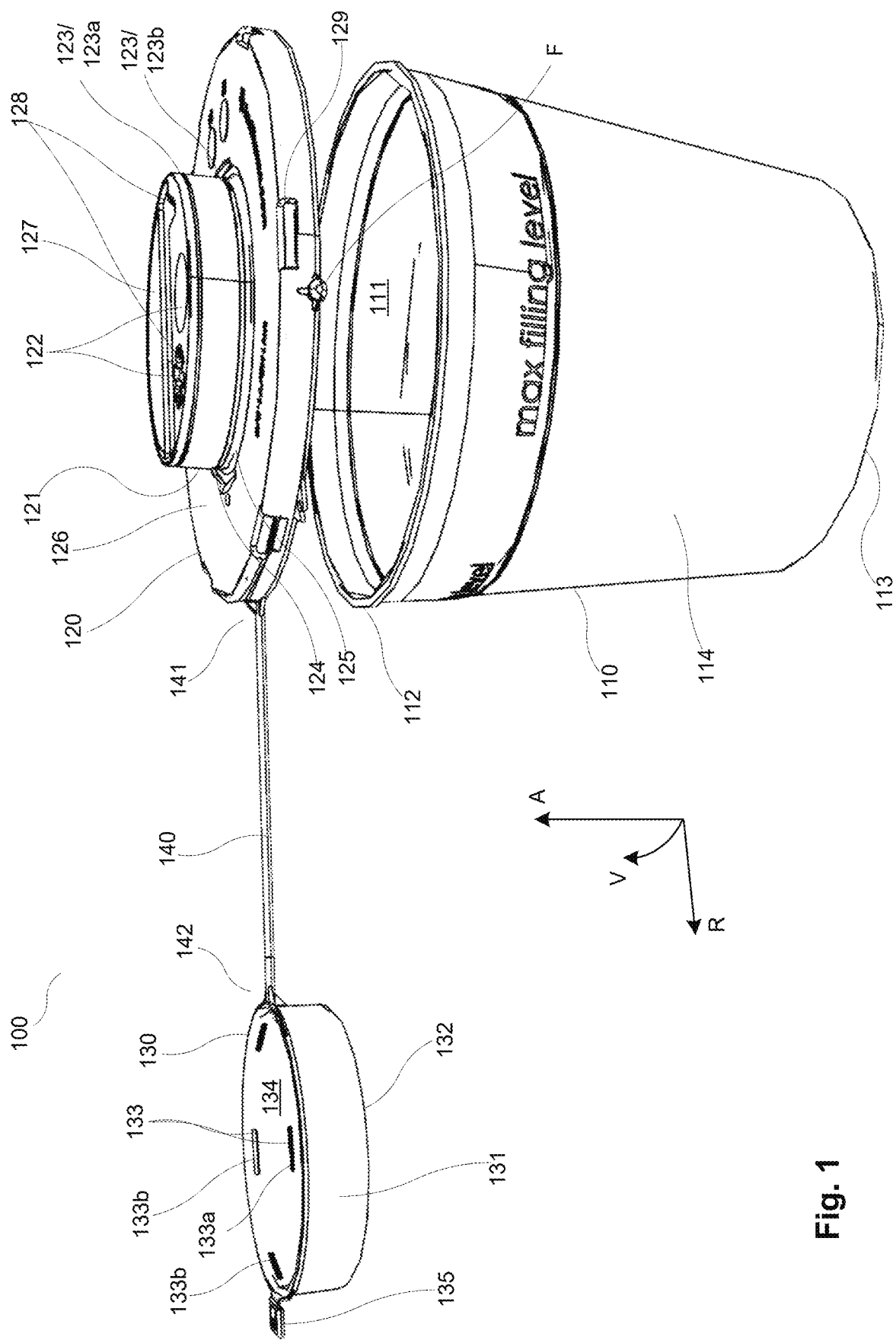
Figure 2:
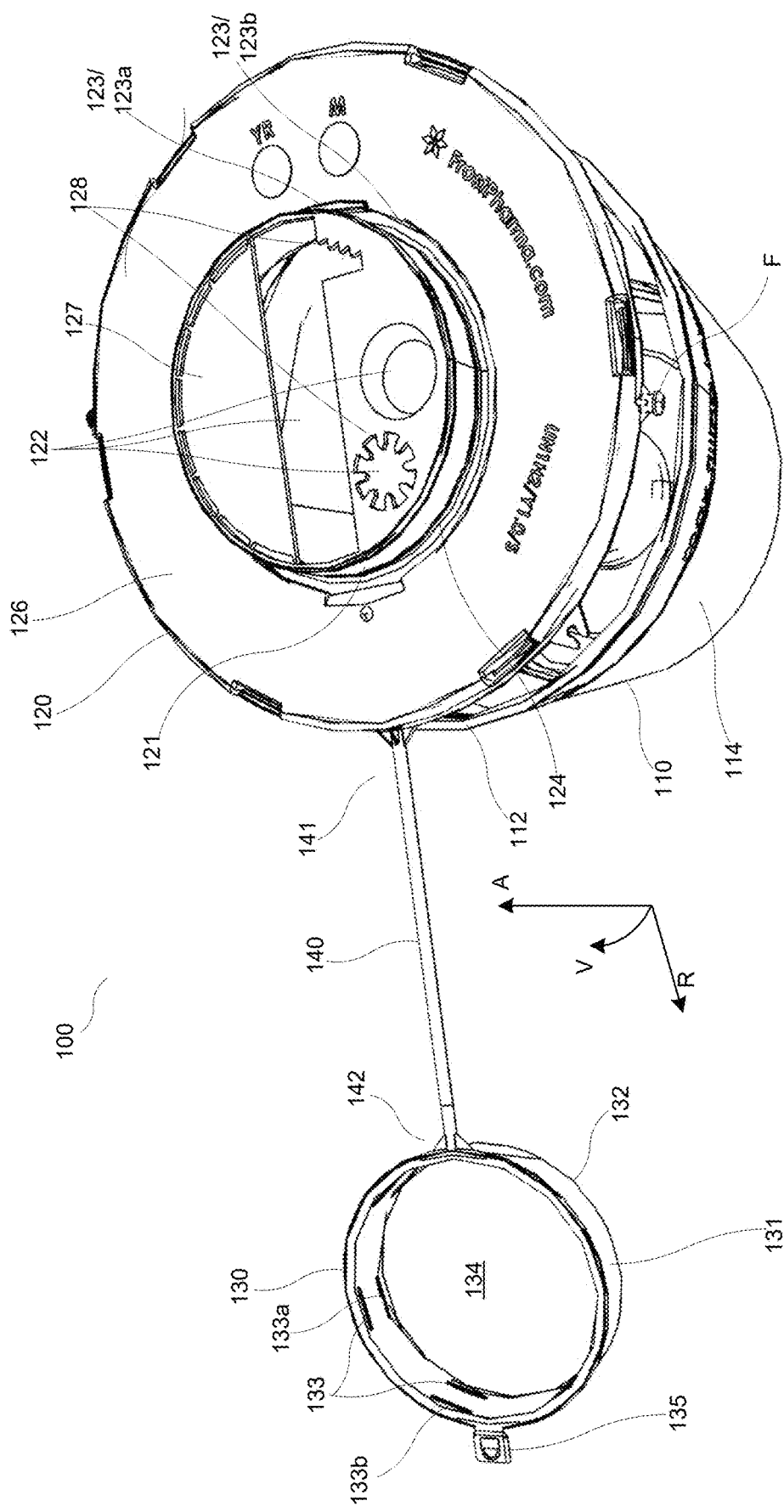
FIGS. 2 and 3 are similar to FIG. 1, but each show the clinical waste container 100 from a different respective perspective.
Figure 3:
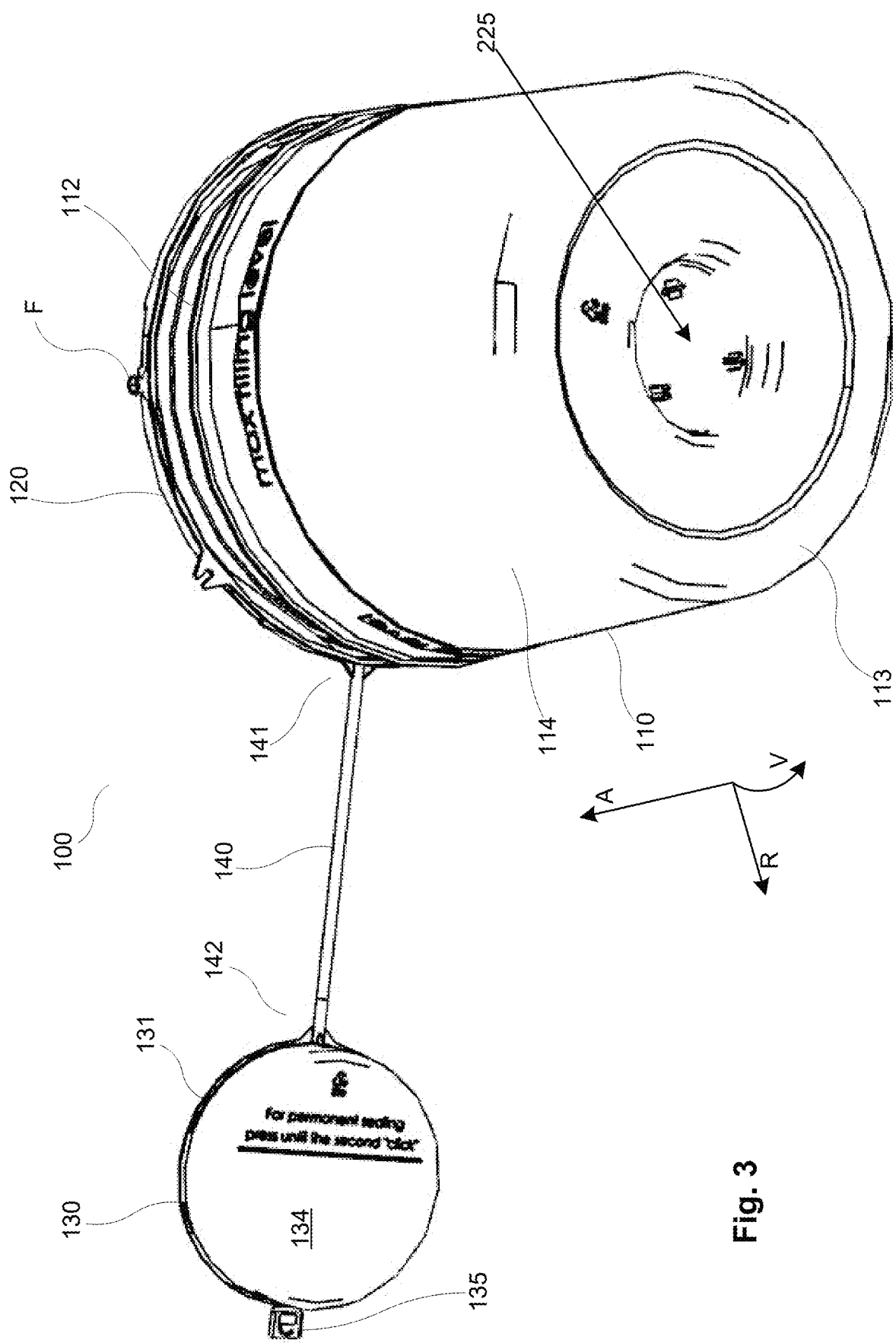
Figure 9:
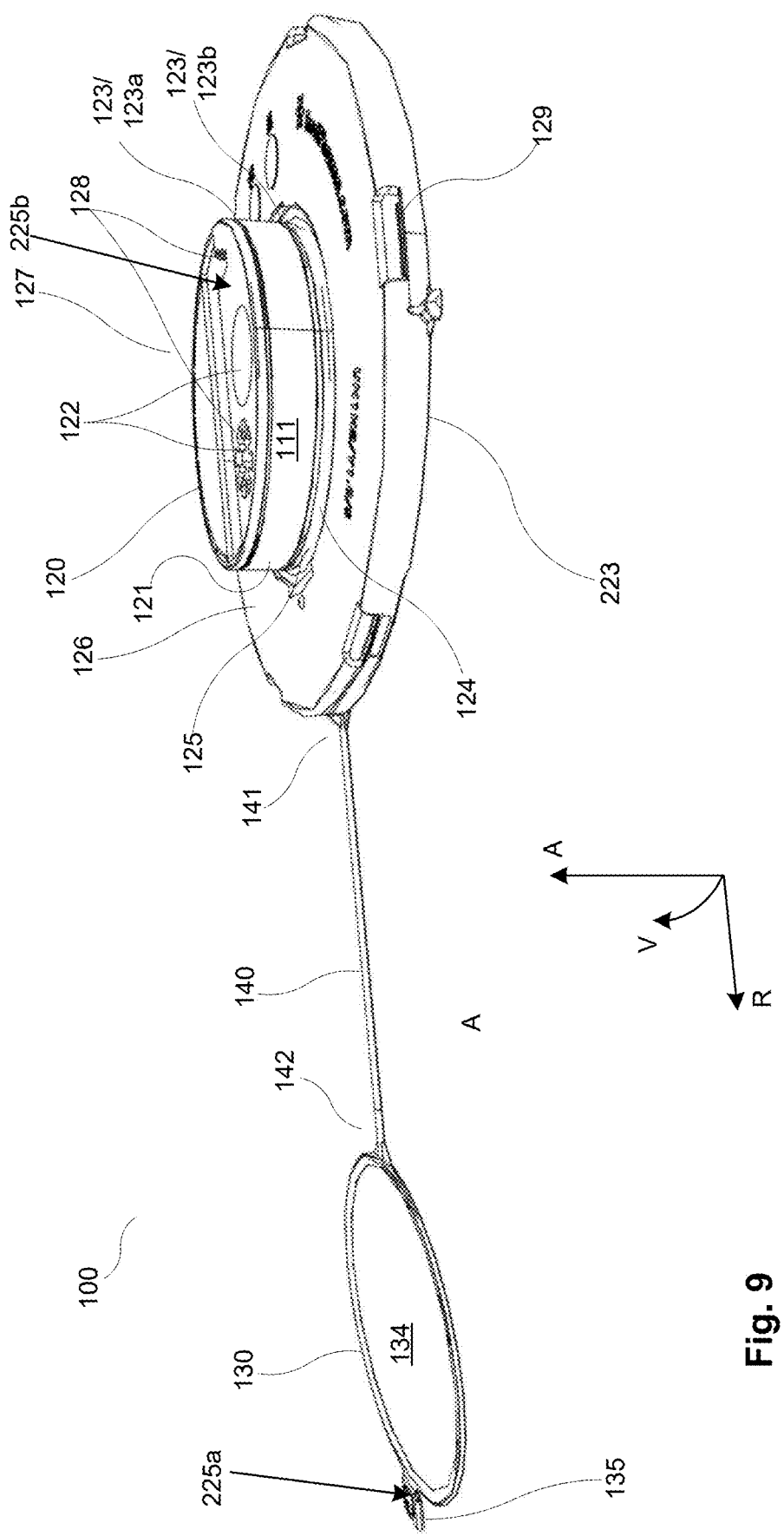

FIG. 9 is a perspective view similar to FIG. 1, but partly removed. Everything below a contact plane 223 has been removed. The contact plane 223 is a plane of contact between two mould parts 221, 222 (not shown in FIG. 9) that together define a mould 220 for making the lid part 120 and the lid cap part 130 as a single, integrated material body, interconnected via the connecting part 140, using injection moulding in a method according to the present invention.

Figure 10:
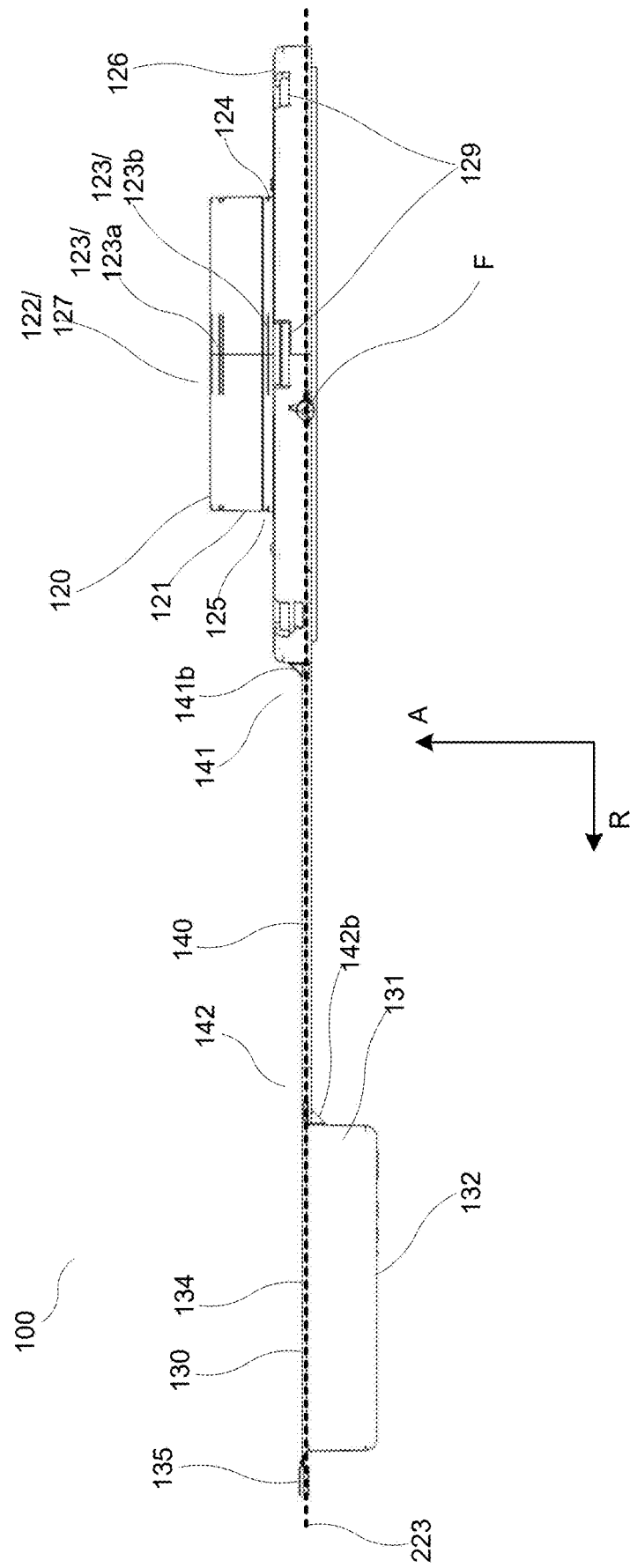

FIG. 10 is a side view of the lid part 120 and the lid cap part 130, further showing said contact plane 223.

FIG. 11 illustrates, in a perspective view, an alternative assembly 300 including a lid part 320, a lid cap part 330 and a connecting part 340.

FIG. 12 is a cross-sectional view illustrating the connecting part 140.

FIG. 13 is a partly removed, cross-sectional view of a mould 200. FIG. 13 shows a mould 200 for making the basket part 110 in a method according to the present invention, but it is realized that a similar mould, perhaps having more than one injection molten plastic point 225, may be used to produce the integrated assembly comprising the lid part 120, the lid cap part 130 and the connecting part 140.

FIG. 14 is a flow chart illustrating a method according to the present invention.

All Figure share the same reference numerals for same or corresponding parts. FIG. 11 uses the same last digits in the reference numerals as FIGS. 1-10 and 12.

Hence, with general reference to the Figures, a clinical waste container 100 is associated, in said upright operating orientation of the clinical waste container 100, with an upwards axial direction A, an outwards radial direction R and an angular direction V. When referring to "upwards" and "downwards" directions for the lid cap part 130, it is assumed that the lid cap part is put onto the lid part 120 (i.e. the connecting part 140 is bent 180°).

The clinical waste container 100 comprises the lower basket part 110, in turn having an upper basket opening 111. The basket part 110 also has a tapered or straight side wall 114.

The clinical waste container 100 also comprises the upper lid part 120, in turn being arranged to be fastened to said basket part 110 so as to cover said basket opening 111. The lid part 120 further comprises a cylindrical part 121 having an upper lid opening 122 arranged to receive clinical waste through said lid opening 122 into said basket part 110.

Even though the clinical waste container 100 is shown as generally circular symmetric in a cross-section taken perpendicularly to the axial direction A, it is realised that the clinical waste container 100 may have other general shapes, such as cross-sectionally square or rectangular, as the case may be. The corresponding also applies to the complementary-shaped cylindrical parts 121, 131 discussed herein. Hence, the cylindrical parts 121, 131 may each be circular-symmetric cylinders or have any other suitable cylindrical shape, as long as they are complementarily shaped so as to achieve a snug fit when the lid cap part 130 is mounted onto the lid part 120 so as to seal the container 100 temporarily or permanently (see below).

Everything which is said regarding the clinical waste container 100 is equally applicable to the assembly 300, as well as to the method of the present invention, and vice versa, as applicable.

The clinical waste container 100 further comprises said lid cap part 130, in turn being arranged to be fastened to said lid part 120 so as to cover said lid opening 122. The lid cap part 130 comprises said cylindrical part 131 having a closed upper end 132 and an inner dimension being larger than an outer dimension of said cylindrical part 121 of the lid part 120. The cylindrical part 131 of the lid cap part 130 is arranged to be slid onto the cylindrical part 121 of the lid part 120 so that the lid cap part 130 as a result covers the lid opening 122. In other words, the cylindrical part 131 of the lid cap part 130 is arranged to at least partly cover the cylindrical part 121 of the lid part 120 when the lid cap part 130 is fully (permanently, see below) mounted onto the lid part 120.

The cylindrical parts 121, 131 may both be slightly cone-shaped to facilitate the sliding of the cylindrical part 131 onto the cylindrical part 121.

The cylindrical part 131 of the lid cap part 130 comprises inner snap-lock means 133, in turn being arranged to engage with outer snap-lock means 123 arranged on the cylindrical part 121 of the lid part 120 so as to fasten the lid cap part 130 on the lid part 120 by the material of at least the lid cap part 130 deforming elastically into a snap-fit lock.

According to the present invention, the lid part 120 and the lid cap part 130 are made from a plastic material comprising at least 30% by volume wooden fibres. The lid part 120 may be made from the same material as the lid cap part 130, in particular in case they are injection moulded as one single, integrated part. The basket 110 may also be made from a plastic material comprising wooden fibres, such as at least 40% by volume wooden fibres.

The remaining material, apart from the wooden fibres, may be a conventional plastic material, such as a conventional thermoplastic, such as polypropylene, or a mixture of such a plastic material with one or several other plastic materials and/or additives. More generally, the remaining material may be any suitable polymer, such as a virgin fossil-based, a recycled fossil-based or a biobased polymer. It is realised that many different such polymers may be suitable for a container of the present type, acting as reinforcement and so providing sufficiently elastic, strong and abrasive-resistant properties to the composite formed when admixing wooden fibres.

Hence, the material used to manufacture the present clinical waste container 100 is a biocomposite material. As an example, a material of the type DuraSense®, marketed by StoraEnso, Sweden, may be used.

Using such a material, the carbon dioxide load of the clinical waste container 100 is significantly reduced, which is advantageous from an environmental point of view.

However, such a material is also significantly less elastic and more brittle as compared to, for instance, polypropylene being a material conventionally used for medical waste containers.

This makes it difficult to design such a clinical waste container 100 that can fulfil all the initially stated requirements on clinical waste containers. This is important, not least since they are often used to transport medical risk waste such as sharp needles and contaminated material.

The present inventors have developed a series of specific design principles that allow a clinical waste container 100 to be manufactured using a biomaterial of the type discussed above without resulting in a quality-wise inferior product.

In the following, these design principles will be described in detail.

Regarding first said inner snap-lock means 133, they may comprise several separated elongated protrusions 133a, 133b, running in the angular direction V in relation to the lid cap part 130 and together defining a broken circle. In other words, there are several discrete such protrusions (in the Figures both an upper series of such discrete protrusions 133a and a lower series of such protrusions 133b), the protrusions belonging to one and the same broken circle being interrupted by stretches without any such protrusion.

Furthermore, the outer snap-lock means 123 may comprise an elongated recess 123a, 123b, running in the angular direction V in relation to the lid part 120 and being arranged to, by at least the material of the lid cap part 130 elastically deforming, engage with said protrusions 133a, 133b by said protrusions 133a, 133b protruding into said recess 123a, 123b along a respective angular V extension of said protrusions 133a, 133b and said recess 123a, 123b, respectively, so as to form a first snap-fit lock, in turn fastening the lid cap part 130 to the lid part 120. In contrast to protrusions 133a, 133b of the inner snap-lock means 133, the elongated recesses 123a, 123b may extend uninterrupted along the full 360° lap in the angular direction V. However, as discussed each of the protrusions 133a, 133b will be interrupted along the angular direction V at least on one location, preferably in at least two locations or even at least in four locations. In the Figures, a preferred embodiment in which each of the protrusions 133a, 133b is interrupted in six locations is shown.

Figure 4:
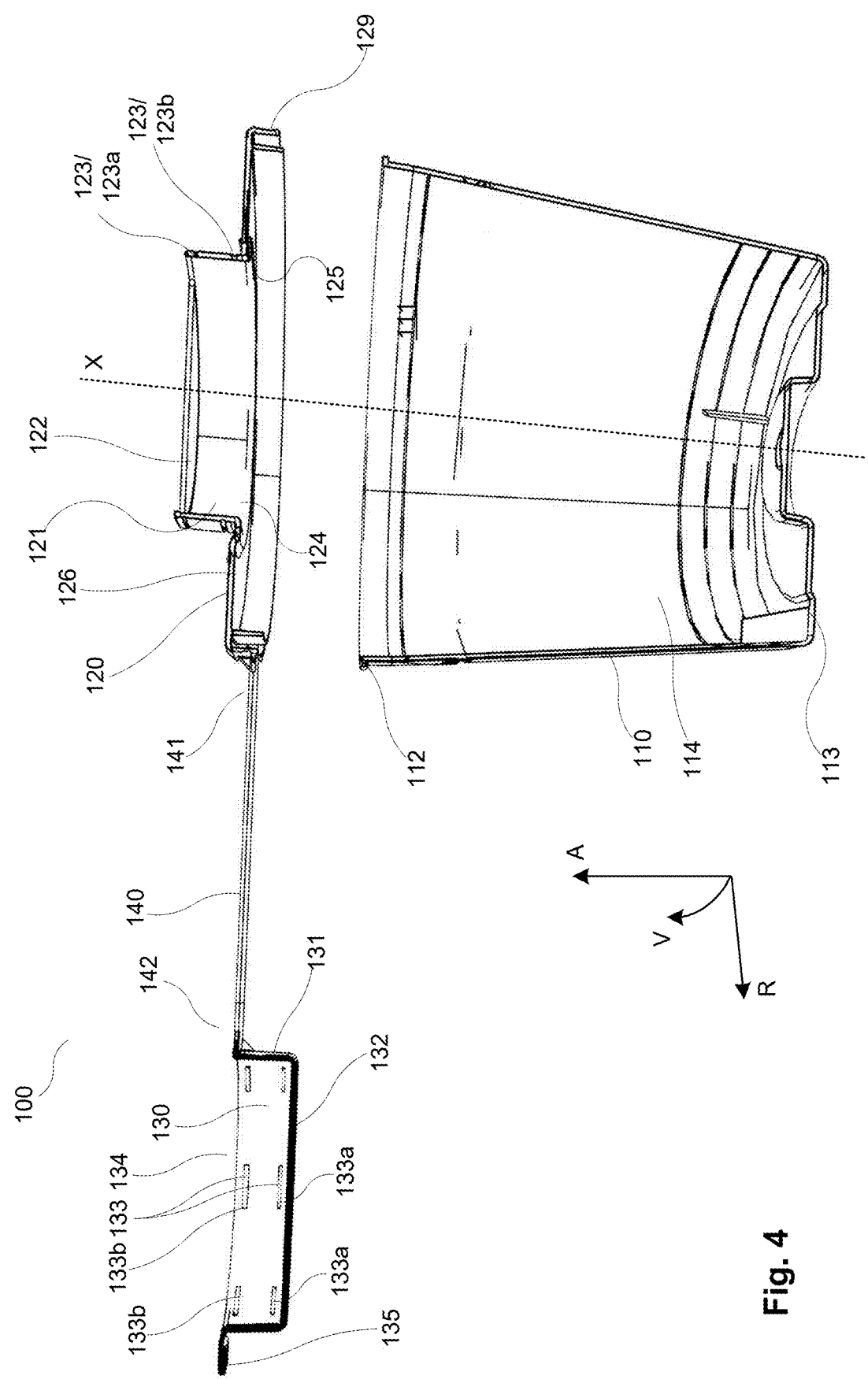
FIG. 4 is also similar to FIG. 1, but shows the clinical waste container 100 partly removed, so that a substantially radially extending cross-section being exposed.
Figure 5:
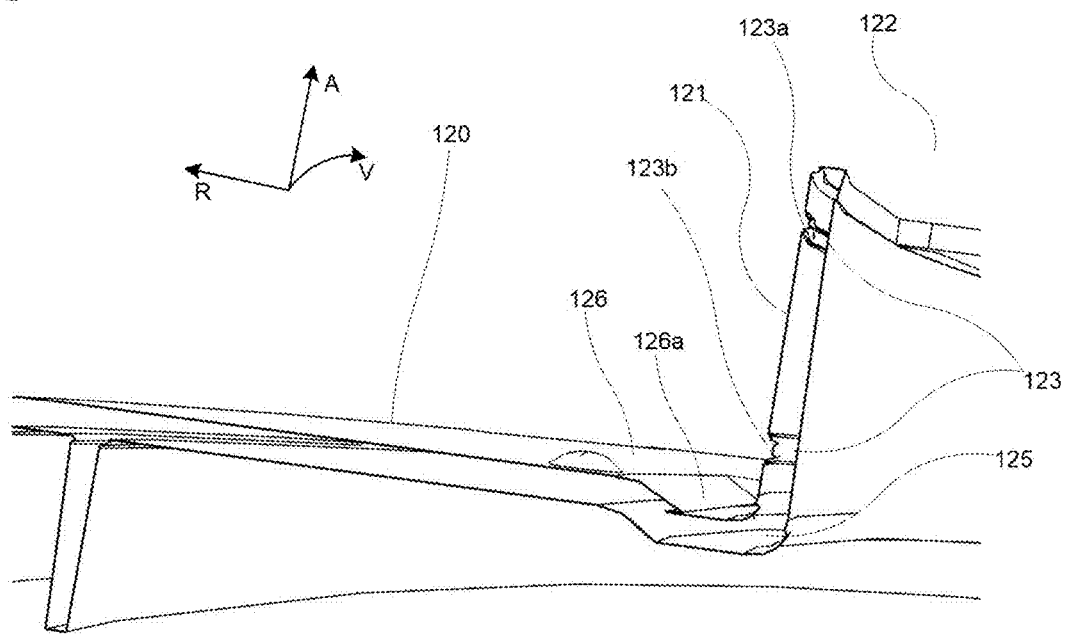
FIG. 5 is a detail view of the clinical waste container 100 shown in FIG. 4, having the same cross-section exposed.
Figure 6:
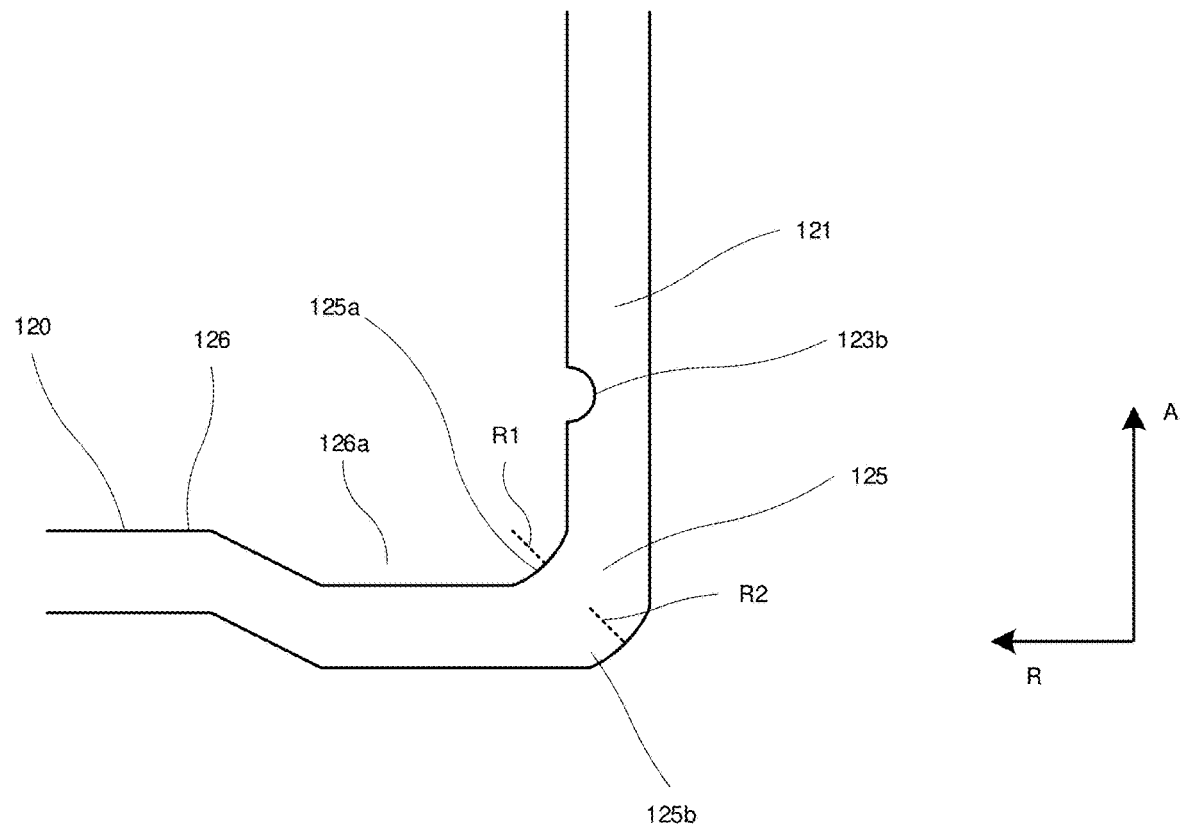
FIG. 6 is a simplified cross-sectional view of a bend 125 of the clinical waste container 100.
Figure 7:
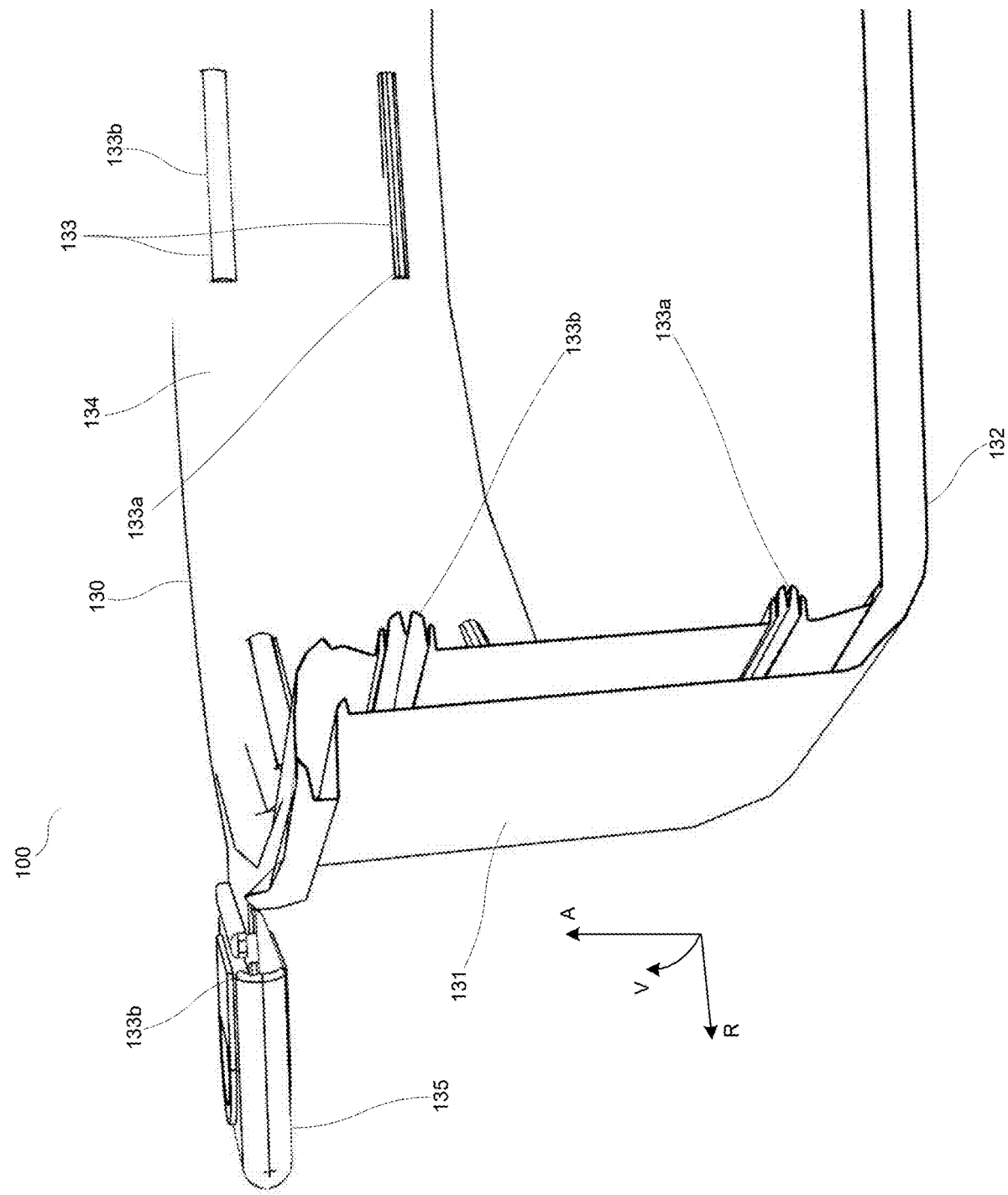
FIG. 7 shows a detail of the lid cap part 130 of the clinical waste container 100, partly removed along a different cross-section.
Figure 8:
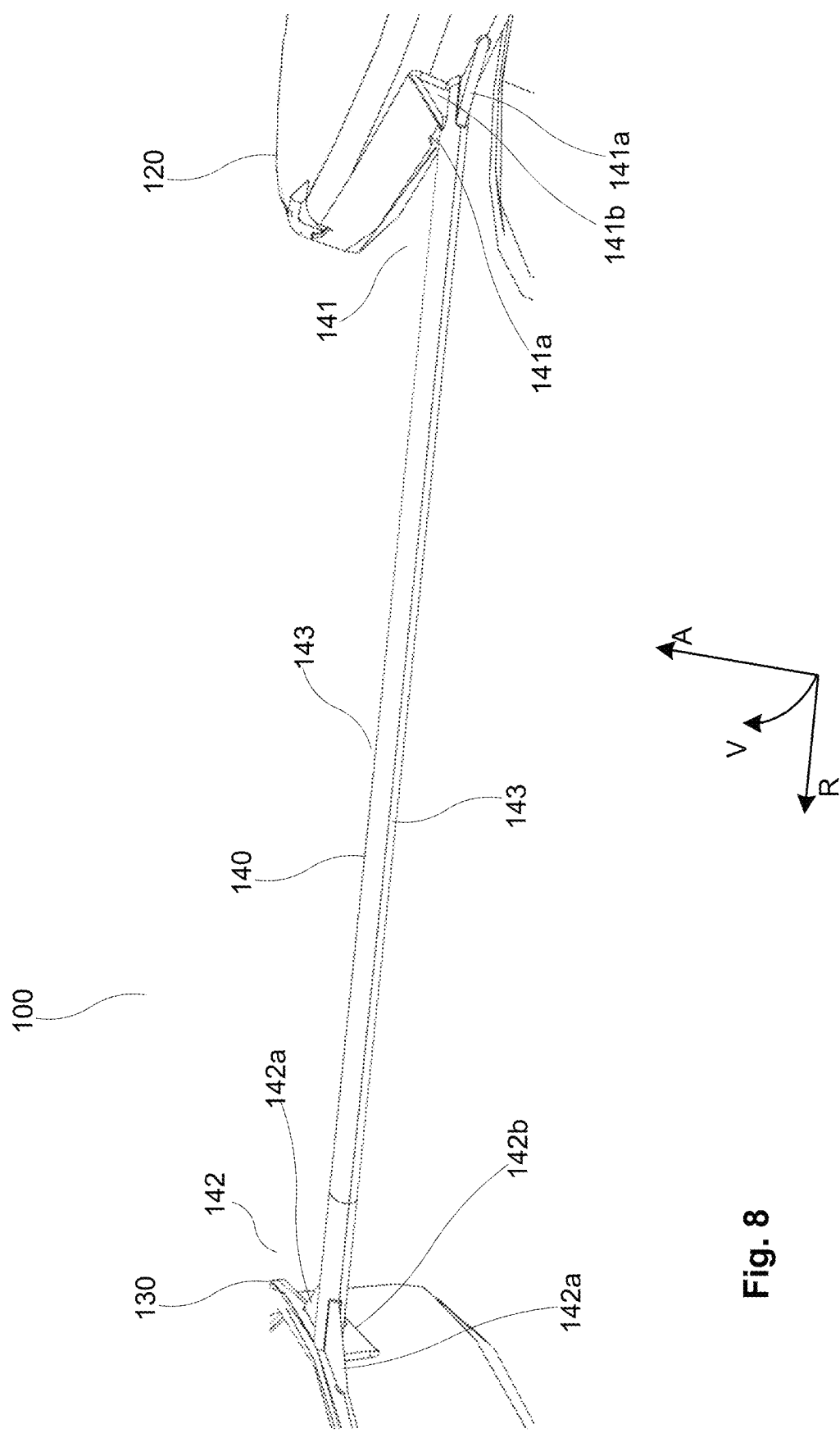
FIG. 8 is a detail of the clinical waste container 100, showing the connecting part 140.

The lid part 120 may comprise, at a lower end 124 of its cylindrical part 121, a bend 125 (see FIGS. 5 and 6) at which bend 125 the cylindrical part 121 of the lid part 120 changes direction at least 60°, such as at least 80°, such as at least locally 85-95°, as seen in a cross-section including an axially A extending centre axis X (see FIG. 4) of the cylindrical part 121 of the lid part 120. An example of such a cross-section is in fact the cross-section at which FIG. 4 is partly removed.

The bend 125 may have a constant cross-section along the full 360° radial direction, or at least along more than 50% of a full lap along the radial direction.

Moreover, the bend 125 may have an inner radius of curvature R1 (see FIG. 6) of at the most 5 mm and an outer radius of curvature R2 of at the most 5 mm.

Furthermore, a material thickness, perpendicularly to opposite sides of the materially as measured locally, of the lid part 120 may be at least 25% thicker locally at said bend 125 as compared to a corresponding material thickness adjacent to the bend 125 in said cylindrical part 121 of the lid part 120.

The locally thickening of the material may be limited to the bend 125 itself, by simply adjusting the radii of curvature R1, R2 as described below, keeping the material thickness uniform or at least substantially uniform (taking into consideration local features, as the case may be) in the rest of the cylindrical part 121 and the cover 126 of the lid part 120.

The present inventors have realised that a design of the lid part 120 and the lid cap part 130 having such cooperating snap-lock means 123, 133, where the inner snap-lock means 133 are arranged in the way described above, forming a respective broken circle in the radial direction, allows for an effective snap-lock both for closing the container 100 temporarily and permanently, and that allows the lid cap part 130 to be injection moulded without being damaged when ejected from the mould once hardened. The local thickness of the bend 125 surprisingly is enough so as to strengthen the lid part 120 to be able to press down the lid cap part 130 with sufficient force so as to engage said snap-lock means 123, 133 with each other. By providing such an only locally increased thickness, the total amount of material used to manufacture the lid part 120 can be kept to a minimum, with a smaller material thickness in the rest of the cylindrical part 121 and the cover 126 than what would otherwise have been the case.

In other words, the presently described combination of the snap-lock means 123, 133 and the locally thicker bend 125 achieves a closing mechanism that works adequately in a lid part-lid part cap assembly that can be produced by rapid injection moulding and without having to use more material than what is necessary.

As mentioned, the material thickness of the lid part 120 at said bend 125 may be locally varied by the inner radius of curvature R1 being sufficiently large in relation to the outer radius of curvature R2. In a particularly simple design, this adaptation of radii of curvature is the only reason for the material thickness to be locally increased, and the respective material surfaces may then be flat outside of an inner curved bend part 125a and an outer curved bend part 125b.

An outside of the lid part 120 at said bend 125 (the outer bend part 125b) may have a part-circular shape in the above-discussed cross-section. Similarly, an inside of the lid part 120 at said bend 125 (the inner bend part 125a) may have a part-circular shape in said cross-section.

Concretely, the material thickness of the lid part 120 adjacent to said bend 125 may be at the most 2 mm, such as at the most 1.8 mm, such as between 1.5 and 1.7 mm, such as about 1.6 mm. The whole lid part 120 may have a substantially uniform material thickness (such as being the same across at least 50% of the total surface of the lid part 120), being as discussed in relation to the material thickness adjacent to the bend 125.

Said inner radius of curvature R1 may be at least 1.2 mm, such as at least 1.3 mm. The inner radius of curvature R1 may be at the most 2.0 mm, such as at the most 1.7 mm. In preferred examples, the inner radius of curvature R1 is about 1.5 mm.

Said outer radius of curvature R2 may be at least 1.7 mm, such as at least 1.8 mm. The outer radius of curvature R2 may be at the most 2.5 mm, such as at the most 2.2 mm. In preferred examples, the outer radius of curvature R2 is about 2.0 mm.

In particular, the material thickness of the lid part 120 at least adjacent to the bend 125, in the cylindrical part 121 and/or the cover 126, may be constant.

The cover 126 is shown in the Figures to be a generally flat part, extending substantially horizontally between the edge of the cylindrical part 121 to a peripheral edge of the lid part 120. It is understood that this cover 126 may have other shapes, but is arranged to cover the basket opening 111 outside of the cylindrical part 121.

In the Figures, the snap-lock means 123, 133 comprise two axially offset outer snap-lock means 123 as well as two axially offset inner snap-lock means 133. In various examples, there may be only one of either one or both of said snap-lock means 123, 133; and/or more than two of either one or both of said snap-lock means 123, 133. At any rate, it is preferred that an axially A lower-most one of the inner snap-lock means 133 is of the type mentioned above, forming a broken circle. It is also preferred that no inner snap-lock means 133 being arranged axially A above another inner snap-lock means 133 is provided as a full circle (360°) protrusion. In case there is only one inner snap-lock means 133, it is preferred that this inner snap-lock means 133 is arranged near the axially A lower end 124 when the lid cap part 130 is fully pushed down onto the lid part 120 cylinder 121, in other words such single inner snap-lock means 133 is provided near the lower opening 134 of the lid cap part 130.

However, and as is illustrated in the Figures, in preferred embodiments the outer snap-lock means 123 may comprise the pair of axially A offset but parallel elongated recesses 123a, 123b on the cylindrical part 121 of the lid part 120.

The inner snap-lock means 133 may comprise the pair of axially A offset but parallel elongated protrusions 133a, 133b on the cylindrical part 131 of the lid cap part 130.

As mentioned, the cylindrical part 131 of the lid cap part 130 may be arranged to be pressed down onto (around) the cylindrical part 121 of the lid part 120 so that an upper one 123a of said recesses engages with a lower one 133b of said protrusions so as to form a snap-fit lock removably sealing the clinical waste container 100 to the lid cap part 130 in an upper position. From this upper position, the lid cap part 130 may be pressed down further onto the lid part 120, but as long as the lid cap part 130 is not fully pressed down it is removable from the lid part 120 by simply pulling the lid cap part 130 upwards.

However, as mentioned the lid cap part 130 may be further arranged be pressed, from said upper position, further down onto to the lid part 120 to a lower position, in which an upper one 123a of said recesses engages with an upper one 133a of said protrusions and in which a lower one 123b of said recesses engages with a lower one 133b of said protrusions so as to form a snap-fit lock permanently sealing the clinical waste container 100 to the lid cap part 130.

In this lower position, it is preferred that a flap 135 of the lid cap part 130 is bent about 90° upwards, from a generally horizontal orientation to a generally vertical orientation, so as to signal that the clinical waste container 100 has been permanently sealed and should be re-opened by brute force.

The lid part 120 comprise a angularly V elongated ditch or recess 126a running around the lower end 124 of the cylindric part 121. In the lower position, it is preferred that a lower end edge of the cylindric part 131 of the lip cap part 130 extends down into, and is received in, said ditch or recess 126a, at a vertical depth in said ditch or recess 126a so that said lower end edge of the cylindric part 131 is located beneath an upper surface of the cover 126 of the lid part 120. The vertical position of the lid cap part 130 in relation to the lid part 120 may be determined based on a relative orientation of the snap-lock means 123, 133 in relation to each other. This way, once the lid cap part 130 has been fully pushed down into the lower position, it is difficult to force the container 100 open again by inserting some kind of lever under the lid cap part 130 cylindric part 131 and bending it open.

At least one of said upper 133a and lower 133b protrusions may then be in the form of several separated elongated protrusions as discussed above, running in the angular direction V in relation to the lid cap part 130 and together defining a broken circle.

Said lower one 133b of said protrusions may be arranged to protrude radially R inwards between 0.3 and 0.5 mm, such as about 0.4 mm from an inner surface of the lid cap part 130.

Said upper one 133a of said protrusions may be arranged to protrude radially R inwards between 0.2 and 0.4 mm, such as about 0.3 mm. At any rate, it is preferred that the upper one 133a of the protrusions protrudes radially inwards R at least 0.05 mm less, such as at least 0.1 mm less, from said inner surface of the lid cap part 130 as compared to said lower one 133a of said protrusions.

As mentioned above, most or even substantially all of the lid part 120 may have a uniform material thickness. Such general material thickness of the lid part 120 may be at the most 2 mm, such as at the most 1.8 mm, such as between 1.5 and 1.7 mm, such as about 1.6 mm. The lid cap part 130 may have a similar or identical general material thickness as the lid part 120.

To the contrary, a corresponding general material thickness of the basket part 110 may be smaller than said general thickness of the lid part 120, such as at least 0.1 or even 0.2 mm smaller. The material thickness of the basket part 110 may be less than 1.7 mm, and it may be more than 1.5 mm. An exception could be in the bottom 113 of the basket part 110, where the material thickness can be larger, such as about 1.8 mm.

The present inventors have realised that using such general material thicknesses in the lid part 120 as compared to in the basket part 110 allows the optimisation of the use of wooden fibres globally in the clinical waste container 100 while still fulfilling the requirements given above. Specifically, the basket part 110 may be made from said plastic material comprising wooden fibres, but comprising a larger share of wooden fibres than the lid part 120 does. This means that the basket part 110 comprises a relatively smaller amount of plastic material (such as polypropylene). Since the basket part 110 contains a smaller volume of material, an overall optimised use of non-fibrous material is achieved, minimising the carbon footprint of the entire container 100.

Particularly in such cases, it is preferred that the basket part 110 comprises a horizontally protruding edge 112 running along its open upper end 111 and arranged to engage with corresponding snap-lock means 129 of the lid part 120 so as to achieve a snap-fit lock of the lid part 120 to the basket part 110, so as to in turn form the clinical waste container 100 in said operating orientation. Then, said horizontally protruding edge 112 has a minimum height of at least 1.5 mm, or even at least 2.0 mm.

As can be viewed in the Figures, the lid part 120 and the lid cap part 130 may be interconnected by a connecting part 140, constituting the same material body as the lid part 120 and the lid cap part 130. Hence, the lid part 120, the connecting part 140 and the lid cap part 130 are injected moulded into one and the same, integrated material body, without any joints. The connecting part 140 preferably has an elongated shape, that may stretch across at least 10 cm and with a maximum cross-sectional diameter of about 5 mm.

In preferred embodiments, the connecting part 140 is connected to a lower end of the lid part 120 and to a lower end of the lid cap part 130, when the clinical waste container 100 is in said upright operating orientation and the lid cap part 130 is mounted on the lid part 120, covering the lid opening 122, in which upright operating orientation the connecting part 140 is forced to bend (be bent) elastically at least 1500 or, in the examples shown in the Figures, 180°, as a result of the lid cap part 130 being brought onto the lid opening 122.

As illustrated in the Figures, the connecting part 140 may be arranged to protrude horizontally from the lid part 120, at a proximal end 141 of the connecting part 140, and/or horizontally from the lid cap part 130, at a distal end 142 of the connecting part 140, when in a relaxed state and the clinical waste container 100 is in said upright operating orientation.

As illustrated in FIG. 10, a contact plane 223 between a pair of mould parts 221, 222 used together to make the lid part 120 and the lid cap part 130 in an injection moulding process of the type described below, runs through said lower end of the lid cap part 130, through said lower end of the lid part 120 and through the connecting part 140, effectively splitting the material body in question in exactly two parts. The top one of these parts is shown in FIG. 9. Using two injection locations, as described below, will efficiently fill such a structure with the presently used plastic material, in particular when using the material sizes and so forth described herein. The contact plane 223 may be planar, in other words not bent or curved.

As mentioned, the connecting part 140 may be elongated, and may in cross-section (the cross-section being perpendicular to a man longitudinal direction of the connecting part 140) comprise a pair of likewise elongated wing-like protrusions 143 extending on and out from either horizontal lateral sides of the connecting part 140 when the clinical waste container 100 is in said upright operating orientation. This is perhaps best seen in FIG. 12.

In some embodiments, each of a connection point between the connecting part 140 and the lid part 120 (at said proximal end 141) and the lid cap part 130 (at said distal end 142), respectively, comprises two respective horizontal support structures 141a, 142a as well as a respective vertical support structure 141b, 142b.

Said horizontal support structures 141a, 142 each may extend in either lateral (horizontal in said operating orientation) direction in relation to the connecting part 140. Each of said support structures 141a, 141b, 142a, 142b may interconnect a respective lateral side of the connecting part 140 to an outside surface of the lid part 120 or lid cap part 130, respectively. Each of said support structures 141a, 141b, 142a, 142b may be triangular, as illustrated in the Figures, or have any other suitable shape. Preferably however, they interconnects a point at least 3 mm along the connecting part 140 end, from said side surface in question, with a point at least 3 mm from the connecting part 140 on said side surface in question, so as to achieve a strengthening of the connection between the connecting part 140 to the surface side (of the lid part 120 or the lid cap part 130) in question.

In particular in case the contact plane 223 is arranged in relation to the lid part 120 and the lid cap part 130 as has been described above, it is preferred that the vertical support part 141b interconnecting the connecting part 140 to the lid part 120 extends upwards from the connecting part 140, while the vertical support part 142b interconnecting the connecting part 140 to the lid cap part 130 extends downwards from the connecting part 140, when the clinic waste container 100 is in its operating orientation and in a relaxed state of the connecting part 140. See FIG. 10.

This achieves a number of effects. Firstly, the structure can be efficiently filled during injection moulding. Secondly, the positioning of the contact plane 223 is optimal in terms of structural strength of both the lid part 120 and the lid cap part 130. Thirdly, the connection between the connecting part 140 and the lid part 120 and the lid cap part 130, respectively, is achieved that has sufficient strength to withstand the strain accruing when the connecting part 140 is bent to bringing the lid cap part 130 onto the cap part 120, even as it is manufactured from the above discussed relatively brittle material.

As shown in the Figures, the lid part 120 opening 122 may comprise an interface 127 for item disposal, that may for instance comprise a syringe needle or blade disconnector means 128, which in turn may be of standard type.

The Figures also show a fastening means F, in the form of a small head-shaped form. If a handle is needed to carry the container 100, a flexible string may be attached on either side of the lid part 120, to a respective such fastening means F.

The basket part 110 may hold a maximum volume of, for instance, at least 2 liters, and it may hold a maximum volume of, for instance, at the most 5 liters. By varying the height of the basket part 110, the total volume of the container 100 may be varied while using one and the same lid part 120 and one and the same lid cap part 130.

FIG. 11 illustrates an alternative lid part 320/lid cap part 330/connecting part 340 configuration, that is generally similar to the configuration illustrated in FIGS. 1-10.

FIG. 14 illustrates a method according to the present invention, for producing a clinical waste container 100 of the type described herein.

In a first step, the method starts.

In a subsequent step, a metal mould 220 is provided, together with a heated injection nozzle 210. The nozzle 210 may for part of the mould 220, and may be separately heated, such as using electric resistance cables arranged in or on the nozzle 210, as is conventional as such. The nozzle is arranged to delivery molten plastic material to a respective injection point in the mould. In case there are more than one such injection points, there is one nozzle per such injection point.

FIG. 13 illustrates such a mould 220, with such an injection nozzle 210. It is realised that the exemplifying mould 220 shown in FIG. 13 is a mould for producing the basket part 110, but a similar mould 220 will be used to produce either of the lid part 220, 420 variants.

For the lid part 220, 420, two injection points may be used, as will be described below.

In a subsequent step, molten plastic material is injected via the heated nozzle 210 into the mould 220, the molten plastic material comprising at least 30% by volume wooden fibres as described above.

In a subsequent step, the plastic material is allowed to harden by cooling to form said basket part 110, said lid part 120, said lid cap part 130, and/or said connecting part 140, as the case may be.

In a subsequent step, the part in question is removed from the mould 220. For the lid cap part 130, a per-se conventional ejector mechanism is used to eject the lid cap part 130 from the mould, the disjoint ridges of the inner snap-lock means 133 will not be damaged since they allow elastic deformation of the moulded material without breaking.

At least the lid part 120 and the lid cap part 130 is manufactured in this manner.

In a subsequent step, the basket part 110 is provided, potentially using injection moulding in the corresponding manner of the basket part 110.

In a subsequent step, the lid part 120 may be mounted onto the basket part 110 so as to form the final clinical waste container 100.

In a subsequent step, the method ends.

The present inventors have realised that good results are achieved in case said mould 220 and said heated nozzle 210 are both made from a stainless steel material comprising at least 12% chromium, such as about 13% chromium, and which stainless steel material is hardened to at least 50 HRC (Rockwell scale). One example of a suitable material is S50C 1.2083 steel. Such material will withstand both abrasive wear and the relatively aggressive chemical environment presented by the present molten material.

In the above-described preferred case in which the mould 220 defines the shape of the lid part 120 and the lid cap part 130 as a connected body being connected by the connecting part 140, and wherein both the lid part 120 and the lid cap part 130 are formed by said injection of said molten plastic material into said mould 220, the molten plastic may advantageously be injected into the mould 220 at two different injection points 225a, 225b (see FIG. 9), one on the lid part 120 and another one on the lid cap part 130 (which may be at the flap 134).

As for the basket part 110, a single injection point 225 may be arranged in the bottom 113 of the basket part 110.

As discussed above, the contact plane 223 between the first mould part 221 and the second mould part 222 (the first 221 and second 222 mould parts forming said mould 220 in a mounted state) may be flat (planar) and may pass through said lid part 120, through said connecting part 140 and through said lid cap part 130.

In this case, the contact plane 223 may be horizontal when the lid part 120 is in said upright operating orientation. Also, the lid part 120 may in this case protrude mainly on a first side (an upper side in FIG. 10) of the contact plane 223, whereas the lid cap part 130 may protrude mainly on a second side (a lower side in FIG. 10) of the contact plane 223.

As is illustrated in FIG. 13, the mould may contain integrated cooling channels 234, through which a cooling fluid (such as water) may be circulated so as to cool the mould 220 to a desired temperature during moulding.

The present inventors have realised that a relatively high cooling temperature is suitable to achieve the present goals. Hence, the method may further comprise actively and continuously cooling the mould 220, using said cooling fluid circulating in said channels 234 through the mould 220, during the hardening of the plastic material, to a constant temperature of at least 30° C., such as at least 40° C. or even at least 50° C., during the whole moulding process.

Such a moulding process of a container 100, 300 of the above-described type, with the features described herein, achieves that full plastic injection can be achieved in a quick and efficient production process, resulting in a sufficiently durable container 100, 300 that achieves a significant lowering of its carbon footprint as compared to conventional clinical waste containers.

Above, preferred embodiments have been described. However, it is apparent to the skilled person that many modifications can be made to the disclosed embodiments without departing from the basic idea of the invention.

It is generally realised that the inventive effort underlying the present invention is to make a series of modifications to a conventional clinical waste container so as to allow the present biocomposite to be used instead of, for instance, 100% polypropylene. Herein, a number of such specific modifications have been described, and various ways of combining such modifications. It is, however, realised that the modifications and features described herein can be combined also in other ways, as the case may be.

Hence, the invention is not limited to the described embodiments, but can be varied within the scope of the enclosed claims.

The invention claimed is:

1. A method for producing a clinical waste container, the clinical waste container being associated, in an upright operating orientation of the clinical waste container, with an upwards axial direction, an outwards radial direction and an angular direction, the clinical waste container comprising
    a lower basket part, having an upper basket opening; and
    an upper lid part, arranged to be fastened to the basket part so as to cover the basket opening, the lid part comprising a cylindrical part having an upper lid opening arranged to receive clinical waste through the lid opening into the basket part,
    wherein the method comprises
    providing a metal mold and a heated nozzle;
    injecting molten plastic material comprising at least 30% by volume wooden fibers via the heated nozzle into the mold;
    allowing the plastic material to harden by cooling to form the lid part;
    removing the lid part from the mold; and
    providing the basket part, wherein
    the mold and the heated nozzle are made from a stainless steel material comprising at least 12% chromium and is hardened to at least 50 HRC (Rockwell scale).

2. The method of claim 1, wherein
    the mold and the heated nozzle are made from a stainless steel material comprising about 13% chromium.

3. The method of claim 1, wherein
    the mold and the heated nozzle are made from S50C 1.2083 steel.

4. The method of claim 1, wherein the clinical waste container further comprises
    a lid cap part, arranged to be fastened to the lid part so as to cover the lid opening, the lid cap part comprising a cylindrical part having a closed upper end and an inner dimension being larger than an outer dimension of the cylindrical part of the lid part, the cylindrical part of the lid cap part being arranged to be slid onto the cylindrical part of the lid part so that the lid cap part as a result covers the lid opening.

5. The method of claim 4, wherein
    the cylindrical part of the lid cap part comprises inner snap-lock means arranged to engage with outer snap-lock means arranged on the cylindrical part of the lid part so as to fasten the lid cap part on the lid part by the material of at least the lid cap part deforming elastically into a snap-fit lock.

6. The method of claim 5, wherein
    the inner snap-lock means comprises several separated elongated protrusions, running in the angular direction in relation to the lid cap part and together defining a broken circle, and wherein the method further comprises
    removing the lid cap part from the mold by ejection.

7. The method of claim 1, wherein
    the molten plastic is injected into the mold at two different injection points, and wherein the method comprises using one heated nozzle per such injection point.

8. The method of claim 4, wherein
    the mold defines the shape of the lid part and the lid cap as a connected body being connected by a connecting part, both the lid part and the lid cap part being formed by the injection of the molten plastic material into the mold, and wherein the molten plastic is injected into the mold at two different injection points, one on the lid part and another one on the lid cap part.

9. The method of claim 8, wherein a contact plane between a first mold part and a second mold part, the first and second mold parts forming the mold in a mounted state, is flat and passes through the lid part, the connecting part and the lid cap part, wherein the contact plane is horizontal when the lid part is in the upright operating orientation, wherein the lid part protrudes mainly on a first side of the contact plane and the lid cap part protrudes mainly on a second side of the contact plane.

10. The method of claim 1, wherein the method further comprising actively and continuously cooling the mold, using a cooling fluid circulating in channels through the mold, during the hardening of the plastic material to a constant temperature of at least 30° C.

11. The method of claim 1, wherein at least 50% of the total surface of the lid part has a uniform material thickness.

12. The method of claim 1, wherein a material thickness of the lid part is at the most 2 mm.

\* \* \* \* \*